(12) United States Patent
Zeng et al.

(10) Patent No.: US 8,968,205 B2
(45) Date of Patent: Mar. 3, 2015

(54) SUB-APERTURE CONTROL IN HIGH INTENSITY FOCUSED ULTRASOUND

(75) Inventors: Xiaozheng Zeng, Sammamish, WA (US); Kevin Michael Sekins, Yarrow Point, CA (US); Stephen Barnes, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 459 days.

(21) Appl. No.: 13/024,574

(22) Filed: Feb. 10, 2011

(65) Prior Publication Data

US 2012/0209150 A1    Aug. 16, 2012

(51) Int. Cl.
*A61B 8/14*    (2006.01)
*A61N 7/02*    (2006.01)
*A61N 7/00*    (2006.01)

(52) U.S. Cl.
CPC ........... *A61N 7/02* (2013.01); *A61N 2007/0052* (2013.01); *A61N 2007/0078* (2013.01); *A61N 2007/0095* (2013.01); *A61N 2007/027* (2013.01)
USPC ............... 600/459; 601/2; 600/437; 600/447; 600/443; 600/444; 367/103

(58) Field of Classification Search
None
See application file for complete search history.

(56) References Cited

U.S. PATENT DOCUMENTS

| | | | | |
|---|---|---|---|---|
| 5,443,071 A | * | 8/1995 | Banjanin et al. | 600/455 |
| 5,570,691 A | * | 11/1996 | Wright et al. | 600/447 |
| 5,573,001 A | * | 11/1996 | Petrofsky et al. | 600/447 |
| 5,617,862 A | * | 4/1997 | Cole et al. | 600/459 |
| 5,676,147 A | * | 10/1997 | Petrofsky et al. | 600/447 |
| 5,784,336 A | * | 7/1998 | Gopinathan et al. | 367/123 |
| 6,029,116 A | * | 2/2000 | Wright et al. | 702/32 |
| 6,193,659 B1 | * | 2/2001 | Ramamurthy et al. | 600/443 |
| 6,221,018 B1 | * | 4/2001 | Ramamurthy et al. | 600/443 |
| 6,482,160 B1 | * | 11/2002 | Stergiopoulos et al. | 600/443 |
| 6,508,774 B1 | * | 1/2003 | Acker et al. | 601/2 |
| 6,682,483 B1 | * | 1/2004 | Abend et al. | 600/437 |
| 6,719,696 B2 | * | 4/2004 | Stergiopoulos et al. | 600/443 |
| 6,773,408 B1 | | 8/2004 | Acker et al. | |

(Continued)

FOREIGN PATENT DOCUMENTS

WO    WO 2007/069157    6/2007
WO    WO 2011/156624    12/2011

OTHER PUBLICATIONS

U.S. Appl. No. 12/554,749, filed Sep. 4, 2009.
(Continued)

*Primary Examiner* — Nicholas Evoy

(57) ABSTRACT

Sub-aperture control is provided for high intensity focused ultrasound. Test transmissions are made sequentially from different sub-apertures. The tissue response at the focal regions is determined and used to select sub-apertures. For example, one or more sub-apertures are not used where temperature does not rise above certain threshold or tissue displacement is weak, such as associated with intervening bone or attenuating tissue. Other factors may be used instead or in addition to tissue response at the focal region. Relative proximity of the sub-apertures to a lesion, angular distribution of the sub-apertures, shape or size of the sub-aperture focal regions as compared to the tissue to be treated, or combinations thereof may be used. Once selected, the relative weight for each sub-aperture may be adjusted based on measured tissue response for each sub-aperture, such as to provide more equal treatment contribution from different sub-apertures.

7 Claims, 2 Drawing Sheets

(56) References Cited

U.S. PATENT DOCUMENTS

| | | | |
|---|---|---|---|
| 7,238,158 B2* | 7/2007 | Abend | 600/454 |
| 7,273,455 B2* | 9/2007 | Angelsen et al. | 600/437 |
| 7,285,094 B2* | 10/2007 | Nohara et al. | 600/447 |
| 7,338,450 B2* | 3/2008 | Kristoffersen et al. | 600/447 |
| 7,399,279 B2* | 7/2008 | Abend et al. | 600/450 |
| 7,534,209 B2* | 5/2009 | Abend et al. | 600/454 |
| 7,615,015 B2* | 11/2009 | Coleman | 601/3 |
| 7,662,114 B2* | 2/2010 | Seip et al. | 601/2 |
| 7,691,063 B2* | 4/2010 | Peteresen et al. | 600/447 |
| 7,695,438 B2* | 4/2010 | Lazenby et al. | 600/447 |
| 7,775,980 B2* | 8/2010 | Sumi | 600/442 |
| 7,867,166 B2* | 1/2011 | Waag et al. | 600/437 |
| 7,946,180 B2* | 5/2011 | Sumi | 73/789 |
| 8,002,705 B1* | 8/2011 | Napolitano et al. | 600/437 |
| 8,018,010 B2* | 9/2011 | Tigli et al. | 257/416 |
| 8,038,616 B2* | 10/2011 | Angelsen et al. | 600/437 |
| 8,208,995 B2* | 6/2012 | Tearney et al. | 600/476 |
| 8,211,019 B2* | 7/2012 | Sumi | 600/442 |
| 2002/0036446 A1* | 3/2002 | Toda et al. | 310/328 |
| 2003/0065262 A1* | 4/2003 | Stergiopoulos et al. | 600/437 |
| 2003/0163046 A1* | 8/2003 | Nohara et al. | 600/443 |
| 2004/0019278 A1* | 1/2004 | Abend | 600/454 |
| 2004/0220474 A1* | 11/2004 | Abend et al. | 600/437 |
| 2004/0267127 A1* | 12/2004 | Abend et al. | 600/450 |
| 2005/0004461 A1* | 1/2005 | Abend | 600/437 |
| 2005/0033170 A1* | 2/2005 | Angelsen et al. | 600/437 |
| 2005/0107702 A1 | 5/2005 | He et al. | |
| 2005/0148873 A1* | 7/2005 | Petersen et al. | 600/447 |
| 2005/0148874 A1* | 7/2005 | Brock-Fisher et al. | 600/447 |
| 2005/0203392 A1* | 9/2005 | Peteresen et al. | 600/437 |
| 2005/0228277 A1* | 10/2005 | Barnes et al. | 600/437 |
| 2005/0240127 A1 | 10/2005 | Seip et al. | |
| 2005/0267369 A1* | 12/2005 | Lazenby et al. | 600/447 |
| 2005/0277835 A1* | 12/2005 | Angelsen et al. | 600/437 |
| 2005/0288588 A1* | 12/2005 | Weber et al. | 600/447 |
| 2006/0052699 A1* | 3/2006 | Angelsen et al. | 600/437 |
| 2006/0064012 A1* | 3/2006 | Waag et al. | 600/437 |
| 2006/0184036 A1* | 8/2006 | Lazenby | 600/472 |
| 2007/0016022 A1* | 1/2007 | Blalock et al. | 600/437 |
| 2007/0016044 A1* | 1/2007 | Blalock et al. | 600/443 |
| 2007/0106157 A1 | 5/2007 | Kaczkowski et al. | |
| 2007/0167752 A1* | 7/2007 | Proulx et al. | 600/437 |
| 2007/0242567 A1* | 10/2007 | Daft et al. | 367/140 |
| 2008/0139937 A1* | 6/2008 | Nohara et al. | 600/443 |
| 2008/0146938 A1* | 6/2008 | Hazard et al. | 600/462 |
| 2008/0242992 A1* | 10/2008 | Criton | 600/447 |
| 2008/0269609 A1* | 10/2008 | Abend et al. | 600/440 |
| 2009/0024034 A1 | 1/2009 | Moreau-Gobard et al. | |
| 2009/0093720 A1* | 4/2009 | Petersen et al. | 600/447 |
| 2009/0105587 A1* | 4/2009 | Petersen et al. | 600/437 |
| 2009/0141957 A1* | 6/2009 | Yen et al. | 382/131 |
| 2010/0036244 A1* | 2/2010 | Angelsen et al. | 600/438 |
| 2010/0063397 A1* | 3/2010 | Wagner | 600/459 |
| 2011/0172538 A1* | 7/2011 | Sumi | 600/453 |
| 2011/0204893 A1* | 8/2011 | Sumi | 324/318 |
| 2012/0155727 A1* | 6/2012 | Orderud | 382/131 |

OTHER PUBLICATIONS

"Ablathem® HIFU features, treatment procedure and safety feature," http://www.edap-tms.com/en_US/products-services/ablatherm-hifu/ablatherm-hifu-device, accessed Dec. 13, 2010, 6 pages.

"Console, The Sonablate® 500," http://www.focus-surgery.com/console.htm, © 2004-2007, accessed Dec. 13, 2010, 2 pages.

InSightec, "ExAblate Family of Systems," http://www.insightec.com/System-Overview.html, accessed Dec. 13, 2010, 4 pages.

ExAblate OR, The Operating Room of the Future, "Personalized Image Guided Acoustic Surgery for Targeted Results," InSightec Ltd., Tirat Carmel 2010, 2 pages.

Koninklijke Philips Electronics N.V., "Sonalleve MR-HIFU," http://www.healthcare.philips.com/main/products/mri/systems/sonalleve/index.wpd, 2004, accessed Dec. 13, 2010, 2 pages.

Imasonic S.A., "High power and therapeutic ultrasound," http://www.imasonic.com/Medical/TMOverview.php, 2002, accessed Dec. 13, 2010, 3 pages.

G. Fleury, et al., "New piezocomposite transducers for therapeutic ultrasound," $2^{nd}$ International Symposium on Therapeutic Ultrasound, Seattle—31/07, Feb. 8, 2002, 4 pages.

China Medical Technologies, Inc. "FEP-BY High Intensity Focused Ultrasound Therapy System," Beijing Economic-Technological Development Area, Beijing China. accessed Dec. 13, 2010.

Chongqing Haifu (HIFU) Technology Co. Ltd., Haifu Model JC, "Focused Ultrasound Tumor Therapeutic System," http://www.haifu.com.cn/en_main_3_show.asp?ID=70, 2007-2010, accessed Dec. 14, 2010, 2 pages.

John Civale, et al., "The use of a segmented transducer for rib sparing in HIFU treatments," http://www. umbjournal.org/article/S0301-5629(06)01677-2/abstract, Joint Department of Physics, Institute of Cancer Research, Sutton, Surrey, UK, Jun. 8, 2006, 2 pages.

Liu Lin Xiong, et al., "Early Clinical Experience Using High Intensity Focused Ultrasound for Palliation of Inoperable Pancreatic Cancer," *JOP. Journal of the Pancreas*—http://www.joplink.net—vol. 10, No. 2—Mar. 2009 [ISSN 1590-8577], pp. 123-129.

PCT Search Report and Written Opinion in counterpart PCT application No. PCT/US2012/024603, dated Oct. 5, 2012; 12 pages total.

* cited by examiner

SUB-APERTURE CONTROL IN HIGH INTENSITY FOCUSED ULTRASOUND

FEDERALLY SPONSORED RESEARCH OR DEVELOPMENT

The U.S. Government has a paid-up license in this invention and the right in limited circumstances to require the patent owner to license others on reasonable terms as provided by the terms of grant no. DARPA HR0011-08-3-0004, awarded by DARPA.

BACKGROUND

The present embodiments relate to sub-aperture control for high intensity focused ultrasound (HIFU) therapy.

HIFU is used for non-invasive tumor ablation or homeostasis. Uterine fibroids, various bone metastasis, liver, kidney, pancreas, and breast cancers may be treated. Other possible treatments using HIFU include homeostasis of liver and blood vessels.

HIFU may be applied from within the patient, such as using an intracavitary applicator, but these devices are invasive and only applicable to specific organs. Extracorporeal HIFU devices are non-invasive. Existing extracorporeal HIFU devices are typically bowl shaped and contains a limited number of elements. Multiple element HIFU devices have been approved for uterine fibroid treatment. Some extracorporeal HIFU devices may lack flexibility in aperture size and focal depths. One example extracorporeal HIFU device has a 26 cm aperture, consisting of 251 PZT elements with electronic control of the small changes in focus position and mechanical positioning for large changes of the focus position. Another example extracorporeal HIFU device has a 12 cm spherically curved single element mechanically positioned for all focus position and depth adjustments. Another HIFU device contains less than 1000 elements. Typically, the elements are driven with individual phase control to achieve focusing and steering. Some extracorporeal HIFU devices may lack flexibility in aperture size and focal depths.

BRIEF SUMMARY

By way of introduction, the preferred embodiments described below include methods, systems, transducers, arrays, computer readable media, and instructions for sub-aperture control for high intensity focused ultrasound. Test transmissions are made sequentially from different sub-apertures. The tissue response at the focal regions is determined and used to select sub-apertures. For example, one or more sub-apertures are not used where temperature does not rise above certain threshold or tissue displacement is weak, such as associated with intervening bone or attenuating tissue. Other factors may be used instead or in addition to tissue response at the focal region. Relative proximity of the sub-apertures to a lesion, angular distribution of the sub-apertures, shape or size of the sub-aperture focal regions as compared to the tissue to be treated, or combinations thereof may be used. Once selected, the relative weight for each sub-aperture may be adjusted based on measured tissue response for each sub-aperture, such as to provide more equal treatment contribution from different sub-apertures.

In a first aspect, a method is provided for sub-aperture control for high intensity focused ultrasound. A target is identified. At least a first sub-aperture is selected from a plurality of sub-apertures. The selection is a function of a match of a region shape of a focus region provided by the at least first sub-aperture to the target. High intensity focused ultrasound is applied to the target with the at least first sub-aperture and not another of the sub-apertures.

In a second aspect, a system is provided for sub-aperture control for high intensity focused ultrasound. A phased array of elements includes a plurality of phased sub-arrays. A sub-aperture circuit is for activating and deactivating the sub-arrays as sub-apertures of the phased array. A processor is operable to control the sub-aperture circuit to select some of the sub-apertures and not select others of the sub-apertures. The selection is as a function of a measured distribution, at a lesion to be treated, due to transmissions from the sub-apertures.

In a third aspect, a non-transitory computer readable storage medium has stored therein data representing instructions executable by a programmed processor for sub-aperture control for high intensity focused ultrasound. The storage medium includes instructions for selecting a first set of sub-apertures as a subset from a second set of sub-apertures, the selecting being as a function of a spatial proximity of the sub-apertures to a lesion, as a function of an angular distribution of the sub-apertures in the first set to the lesion, or combinations thereof; and using the first set of the sub-apertures for the high intensity focused ultrasound.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
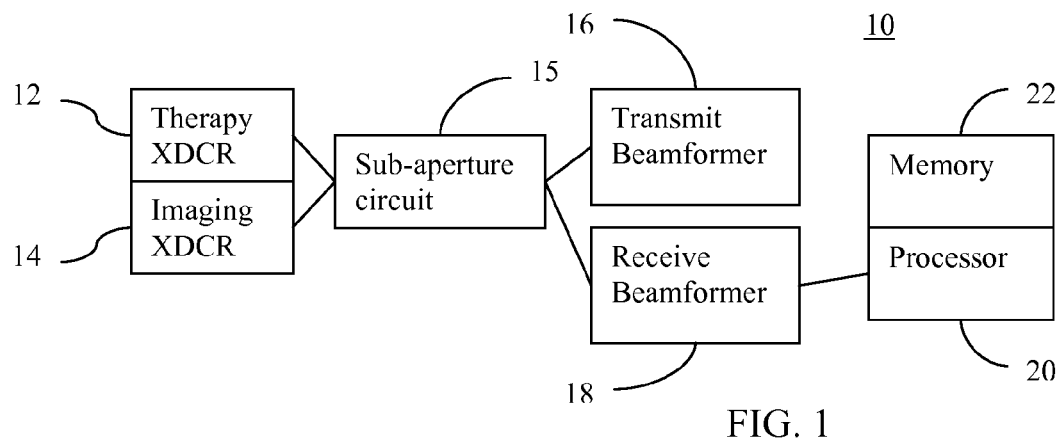
FIG. 1 is a block diagram of one embodiment of a system for sub-aperture control for high intensity focused ultrasound.

An extracorporeal therapeutic ultrasound device includes a continuous or discontinuous array of elements. Sub-apertures of the array may be selectively turned on and the transmit power can be individually controlled by sub-aperture. The sub-apertures may be controlled either coherently (i.e., using the same frequency) or incoherently (i.e., using different frequencies). Sub-apertures are chosen, and therapy dosing is controlled.

Extracorporeal HIFU devices ablate cancerous tissue at a deep site non-invasively. A device with an adaptable transmit aperture ensures an optimal match of the focal region to a target shape while reducing risk of heating healthy tissues.

The target shape may be a lesion or portion of a lesion. Using a controllable aperture of a large number of elements, the aperture size and shape may be tailored according to target size and location, providing more optimal tumor coverage. Portions of the aperture may be de-selected based on available acoustic windows. In the case of occlusions along the acoustic path, an imaging based feedback mechanism may be used to deselect sub-apertures which may be shadowed by the occlusion. Focus size and shape control may also be achieved through manipulating the aperture. Larger or smaller sub-apertures may be used for deeper and shallower targets. Sub-apertures from separate angular spaces may generate crossed beams and produce a spherical focal region to match a spherical lesion, reducing collateral damage.

Sub-apertures are selected based on known characteristics and/or based on measurements in response to testing transmissions. Sub-apertures may be tested individually or simultaneously at a low dose. A tissue temperature or displacement detector may map three-dimensional tissue response to test transmissions. The detected tissue response may be used for selection of sub-apertures and dose. During dosing, feedback from the same temperature or displacement detector may be used to tune dosing parameters on the fly.

In one embodiment, a controller performs auto-selection of sub-apertures based on test transmissions from sub-apertures either sequentially or simultaneously. A low dose shot from each sub-aperture is combined with a tissue temperature/ Acoustic radiation force imaging displacement detector, ultrasound or MRI. The detector determines whether a selected sub-aperture produces a temperature or displacement above a certain threshold. If not above, the sub-aperture is deactivated. With all the selected sub-apertures transmitting at low dose, detected three-dimensional temperature or displacement map may be used to tune each sub-aperture to achieve a desired focus shape.

Sub-apertures are selected for one target lesion, such as portion of a lesion. Alternatively, different sub-apertures may be used simultaneously to treat different targets, such as for the case of multiple shallow targets where only a subset of the overall aperture is needed for each target due to reduced attenuation for shorter beam paths. This approach may speed up the overall treatment time by treating more than one target at a time.

FIG. 1 shows a system 10 for sub-aperture control for high intensity focused ultrasound. The system 10 includes a therapy transducer 12, an imaging transducer 14, a sub-aperture circuit 15, a transmit beamformer 16, a receive beamformer 18, a processor 20, and a memory 22. Additional, different, or fewer components may be used. For example, the therapy and imaging transducers 12, 14 may be a same device. As another example, more transducers of either type may be provided. Only imaging or only therapy transducers 12, 14 may be provided. In another embodiment, only a single transducer array is provided. In another example, a display is provided. Different or the same transmit beamformers 16 may be used for the different types of transducers 12, 14.

In one embodiment, the system 10 is part of an ultrasound imaging and/or therapy system. The system 10 may be for operation with one or more of the transducers 12, 14 internal or external to the patient. A cart imaging system, computer, workstation, or other system may be used. The system 10 may include or have access to information from magnetic resonance imaging (MRI), computer tomography (CT), X-ray, or other imaging systems. In another embodiment, the system 10 is portable, such as for carrying by medics, soldiers, emergency response personnel, or others. The portable system 10 weighs from 1-30 kg.

The transducers 12, 14 are a medical ultrasound transducer. The transducers 12, 14 each include one or more elements. For example, each transducer 12, 14 includes an array of elements.

The therapy transducer 12 is any now known or later developed transducer for generating high intensity focused ultrasound from electrical energy. A plurality of elements in a one or multi-dimensional array may be used, such as an array of N×M elements where both N and M are greater than one for electric based focusing or steering. In one embodiment, only one therapy transducer 12 of a continuous array is provided. In other embodiments, a plurality of therapy transducers 12 is provided. For example, a plurality of two-dimensional arrays of elements is used for transmitting from different locations to a treatment region.

The therapy transducer 12 is configured as a continuous or discontinuous phased array. In one embodiment, the therapy transducer 12 is a concave aperture sub-divided into radial-spaced sectors. The aperture is circular, but may have other shapes. Each sector contains a number of elements operable as a sub-array or sub-aperture. A hollow space is provided in the middle for the imaging array 14.

In another embodiment, the therapy transducer 12 is a concentric ring array. Each ring includes multiple elements. Each ring or group of adjacent rings may be sub-arrays or selectable as sub-apertures. Individual elements or groups of elements in one or more rings may be sub-arrays or selectable as sub-apertures.

Another embodiment is a continuous or discontinuous grouping of a square, rectangular or other shaped sub-arrays in one or more rows and/or columns. Each square, rectangular, or other shaped sub-array is selectable as a sub-aperture. Sub-apertures spanning across and/or using less than all of the elements of two or more sub-arrays may be used. A substantially continuous array may include one or more gaps larger than kerfs or elements separation to provide hinging or flexibility but with a majority of a length including elements.

In one example, the therapy transducer 12 is a conformal phased array. A blanket-like flexible aperture includes a number (e.g., two or more, such as tens) of embedded, rectangular phased arrays. The conformal array may be wrapped around patients. For example, one of conformal or other arrays disclosed in U.S. Published Application Nos. 2008/0183077, 2009/0024034, or 2009/0003675, the disclosures of which are incorporated herein by reference, are used. A blanket, including imaging arrays 14 and therapy transducers 12, is shaped as a cuff, and such may include a balloon or expandable chamber. Alternatively, Velcro® fasteners, zip fasteners, buttons, buckles or other connectors allow adjustable placement of the cuff around limbs or body portions of different sizes. In other embodiments, the blanket conforms to a portion of the body without enclosing or surrounding the portion, such as being a patch that may conform to the torso of a patient. The conformal array flexibly interconnects the transducers 12, 14 and/or elements of a same array.

In another embodiment of a conformal medical ultrasound transducer, a single array conforms by having elements flexibly connected together. A fiber optic or other sensor detects the relative position of elements. Alternatively, the transducer 14 is not flexible or does not conform. Instead, gel and pressure are used to maintain acoustic connection between the transducer 14 and the patient.

The element or elements are piezoelectric, microelectromechanical, or other transducer for converting electrical energy to acoustic energy. For example, the therapy transducer 12 is a capacitive membrane ultrasound transducer.

The therapy transducer 12 is operable from outside a patient. For example, the therapy transducer 12 is a probe or other device held against the patient's skin. The therapy transducer 12 is handheld, positioned by a device, or strapped to the patient. In other embodiments, the therapy transducer 12 is in a probe, catheter or other device for operation from within a patient.

The imaging transducer 14 is the same or different type, material, size, shape, and structure than the therapy transducer 12. For example, each of the one or more imaging transducers 14 includes a multi-dimensional array of capacitive membrane ultrasound transducer elements. The imaging transducer 14 is any now known or later developed transducer for diagnostic ultrasound imaging. The imaging transducer 14 is operable to transmit and receive acoustic energy. In alternative embodiments, no imaging transducer 14 is provided.

The spatial relationship between the transducers 12, 14, elements of an array, and/or different arrays is measurable. For example, pairs of the imaging and therapy transducers 12, 14 are fixedly connected together. A sensor (e.g., a fiber optic, or magnetic) measures the relative position between fixedly connected pairs. As another example, a sensor measures the relative motion between the imaging and therapy transducers 12, 14. In another embodiment, scan data are correlated to determine relative position.

The sub-aperture circuit 15 selects sub-apertures. For example, different sub-arrays are selected. As another example, different groups of elements are selected. The sub-aperture circuit 15 is a multiplexer, digital signal processor, and/or part of the beamformers 16, 18. In one embodiment, the sub-aperture circuit 15 is provided by activating or not activating different channels and by beamforming separately for different channels. For example, a digital signal processor or the beamformers 16, 18 provide signals to and from some arrays in a conformal array and not others, activating some and not activating others. In alternative embodiments, switching is used to select sub-apertures. A multiplexer activates some sub-apertures and not others. The signals from each sub-aperture are beamformed together and separate from the signals of other sub-apertures. The transmit beams are formed separately by sub-aperture, such as by delaying signals relative to each other in a sub-aperture but not across sub-apertures. Even with separate transmit beamforming, signals from one sub-aperture may contribute to other beams from other sub-apertures if transmitted simultaneously.

The transmit beamformer 16 has a plurality of waveform generators, amplifiers, delays, phase rotators, and/or other components. For example, the transmit beamformer 16 has waveform generators for generating square or sinusoidal waves in each of a plurality of channels. The waveform generators or downstream amplifiers set the amplitude of the electrical waveforms. For imaging, the amplitude is set to provide scanning with acoustic beams below any limits on imaging amplitude. The amplitude may be set for high intensity focused ultrasound, such as higher than associated with imaging.

Relative delays and/or phasing of the waveforms focus the transmitted acoustic energy. By applying relatively delayed and/or apodized waveforms to different elements of a transducer, a beam of acoustic energy may be formed with one or more foci along a scan line. The beam has a width (e.g., down 10 dB from a peak) that varies as a function of depth. A focal region is provided, such as a generally elliptical region for HIFU or an elongated linear region for imaging. The focal region is associated with a greater power. Multiple beams may be formed at a same time. For electronic steering, the relative delays establish the beam position and angle relative to the transducer 12, 14. The origin of the beam on the transducer 12, 14 is fixed or may be adjusted by electronic control. For example, the origin may be positioned on different locations on a multi-dimensional array. The different origins result in different positions of the respective beams.

The receive beamformer 18 receives electrical signals from the imaging transducer 14. The electrical signals are from different elements. Using delay and sum beamforming, fast Fourier transform processing, or another process, data representing different spatial locations in a plane or in a volume is formed. One, a few, or many transmission and reception event(s) may be used to scan a volume with the imaging transducer 14. For example, plane wave transmission and reception is used for scanning a volume. Multiple beam reception with or without synthetic beam interpolation may increase the speed of volume scanning with delay and sum beam formation. In alternative embodiments, a two-dimensional plane or scan lines are scanned instead of a three-dimensional volume.

The beamformed data is detected. For example, B-mode detection is provided. In another example, Doppler power, velocity, and/or variance are detected. Any now known or later developed detection may be used. The detected data may be scan converted, remain formatted in the scan format (e.g., polar coordinate), be interpolated to a three-dimensional grid, combinations thereof, or be converted to another format. The detection and/or format conversion are done by separate devices, but may be implemented by the processor 20.

The acquired data may be used for ultrasound thermometry. For example, radio frequency or inphase and quadrature data is analyzed to plan thermometry.

The processor 20 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for controlling the sub-aperture selection circuit 15. In one embodiment, the processor 20 is a controller to perform automatic selection of sub-apertures, such as a beamformer controller, a system controller, sub-aperture circuit controller, a dedicated controller, a general controller, or a system controller. The processor 20 is a single device or multiple devices operating in serial, parallel, or separately. The processor 20 may be a main processor of a computer, such as a laptop or desktop computer, or may be a processor for handling some tasks in a larger system, such as in an imaging system.

The processor 20 controls the sub-aperture circuit 15 to select some of the sub-apertures and not select others of the sub-apertures. The control is through command signals, such as activation signals coded for specific sub-arrays.

Any selection criteria may be used. The paths between the sub-arrays and lesion, the focal region at the lesion, or the position of the sub-arrays relative to the lesion are example criteria. In one embodiment, the type of tissue or other structure along the path is used to determine whether a given sub-array should be used, such as disclosed in U.S. Published Application Nos. 2008/0183077, 2009/0024034, or 2009/0003675. Imaging data may be analyzed to determine the type of tissue and select paths accordingly.

The sub-apertures may be selected based on measured effect at the treatment region. For example, the selection is a function of a measured distribution at a lesion to be treated. The possible therapy sub-apertures transmit a low dose beam which produces a non-lethal temperature rise in the scale of a few degrees or less. Measurements are performed at or around the lesion. Signals returning from the expected focal region are measured. A region larger than the focal region may be measured, such as measuring in a region sufficiently large that likely or possible inaccuracy in predicting the beams focal region places the focal region within the measured region. The measured distribution resulting from the transmission is of focal regions of the sub-apertures. The distribution of effect of the low dose transmission is measured in one, two, or three dimensions.

To better isolate the contribution of each sub-aperture, the test transmissions are performed sequentially. Each sub-aperture or set of sub-apertures transmit in a sequence with a separation interval long enough to allow the tissue response to reach a detectable level. The detectable level may occur more rapidly for tissue displacement measurements than for temperature measurements.

The distribution may be measured by determining a temperature change at different locations in and around the lesion. For example, the temperature change is measured as disclosed in U.S. Published Patent Application No. 2011-0060221 (Ser. No. 12/554,749) and US2007/0106157A1, the disclosure of which are incorporated herein by reference. Instead of temperature change, strain may be detected. Strain is derived from displacement and may be used to estimate temperature.

Anatomy information from an imaging ultrasound scan or MRI, CT, X-ray scans is used with modeling to determine the temperature or other temperature related parameter. The anatomy information may be used to align model features measured from a region. The anatomy information may be used as an input into the model. The anatomy information may be used to select an appropriate model, such as selection based on the type of tissue. The anatomy information may be used to correct an output of the model, such as accounting for temperature distribution due to an adjacent vessel or other conductive tissue.

Locations of greater or greatest temperature change after a given time period may be the focal region for the settings of the transmit beamformer for the sub-aperture. The region associated with a threshold temperature change is treated as the focal region.

In an alternative embodiment, tissue displacement caused by the test transmission is measured. An acoustic transmission may displace tissue, such as associated with ultrasound shear wave or longitudinal wave detection. Acoustic radiation force imaging applies acoustic force to tissue. The low dose signal is the acoustic force radiation, causing the tissue to move. By transmitting from a sub-aperture focused at the lesion, tissue may have greater displacement in or around the lesion. Imaging transmit and receive signals obtained while the tissue returns to steady state may be correlated with signals from the steady state to determine an amount of displacement a certain time after displacement or a sequence of measurements may be used to determine the maximum displacement for each location.

Where there is an obstruction, the temperature, displacement, or other measurement at the focal region may be less than expected or less than a threshold. Sub-apertures associated with measurements below the threshold are not selected and sub-apertures associated with measurements above the threshold are selected. Alternatively or additionally, only a certain number of sub-apertures is selected, so the sub-apertures associated with the greatest measurements are selected. The measured distribution may be used to select sub-apertures based on the lesion. The distributions covering with minimal extent beyond the lesion, individually or as a group, may be selected. Sub-apertures with distribution more beyond the lesion than other sub-apertures may not be selected.

In addition or as an alternative to using test transmissions, the sub-apertures are selected as a function of a proximity of each of the sub-apertures to the lesion. Sub-apertures closer to the lesion may be selected to avoid or minimize harm to tissue from high power transmissions over longer paths. For closer lesions, fewer sub-apertures may be selected since less attenuation occurs. Larger overall apertures may be used for deeper lesions.

An angle distribution of the sub-apertures relative to the lesion may be used for selecting the sub-apertures. By spacing the selected sub-apertures around a greater angle of incidence, less collateral damage may result. The beams from the different sub-apertures cross from different directions, so there is less overlap of beams and less treatment level power outside the lesion. One or more sub-apertures or other amount of space between selected sub-apertures may reduce collateral damage. Another benefit of selecting sub-apertures according to the angular distribution is better control of focus shape. For example, superposed beams from widely spread sub-apertures in angular space produces a relatively symmetric focus.

In one embodiment, the shape of the target without feedback or test measurements is used to select sub-apertures. The focal region of each sub-aperture is estimated, such as estimating based on the F# or other transmit parameters defining the beam. The combination of sub-apertures providing the greatest coverage of the lesion or portion of the lesion while minimizing overlap outside the lesion is used. In another embodiment, the estimated input power from the sub-apertures, absorbed power at the lesion location, and entrance power at the skin surface are used to select sub-apertures. For example, the required total power determines the aperture surface area and power density to be used. The skin burn threshold constrains the minimum aperture area to be recruited.

The processor 20 may also be used to weight contribution from selected sub-apertures. The sub-aperture circuit 15 or the transmit beamformer 16 may be controlled to weight the power. The frequency, number of cycles, amplitude, sub-aperture size, and/or other characteristic of the transmitted waveforms for a HIFU beam are altered to adjust relative contribution. The power from one sub-aperture may be increased or decreased while adjustments are not made to another sub-aperture. Alternatively, adjustments are made to all the sub-apertures. Changing the power provided by one or more sub-apertures may alter the relative contribution.

Differences in distance, attenuation, sub-aperture size, or obstructions may cause some sub-apertures to apply more power to the lesion during treatment than other sub-apertures. While these differences may be acceptable, providing more equal contribution from spatially diverse sub-apertures may create a more spherical lesion and collateral damage may be reduced.

The relative contribution may be predicted, such as using a model based on tissue characteristics. Alternatively, the relative contribution is measured. The measured distributions from testing individual sub-apertures may be used. In other embodiments, all the selected sub-apertures simultaneously transmit test signals. The effect at the lesion or around the lesion is measured, such as measuring the temperature or displacement. Whether individually or together, the spatial distribution of the effect may indicate one or more sub-apertures with greater contribution. For example, the shape of the detected focal region may be elongated along paths from one or more sub-apertures, indicating greater power from those sub-apertures. The power of those sub-apertures may be reduced or the power of the other sub-apertures may be increased to better match the lesion shape. The processor 20 weights the relative power as a function of the measured distribution.

The processor 20 or a different processor may perform other acts. Other possible acts include determining positions of the transducers 12, 14 relative to each other and/or the lesion, aligning and compounding image data, determining paths (e.g., origin on sub-apertures), estimating tissue type, applying models, determining dosing sequence and amount, and/or determining a power, frequency, or other characteristic of the transmitted high intensity focused ultrasound.

The memory 22 stores the ultrasound data for image processing, such as storing data for determining temperature and/or tissue displacement. Alternatively or additionally, the memory 22 stores information and instructions for programming the processor 20 for sub-aperture control for high intensity focused ultrasound. Information to be used include input and output power relationship, steering directivity, estimated size of focus regions at different depths and frequencies, and other characteristics from each sub-aperture. Look-up tables of pre-computed or estimated sub-aperture characteristics may be used by the processor 20.

The instructions for implementing the processes, methods and/or techniques discussed above are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 2:
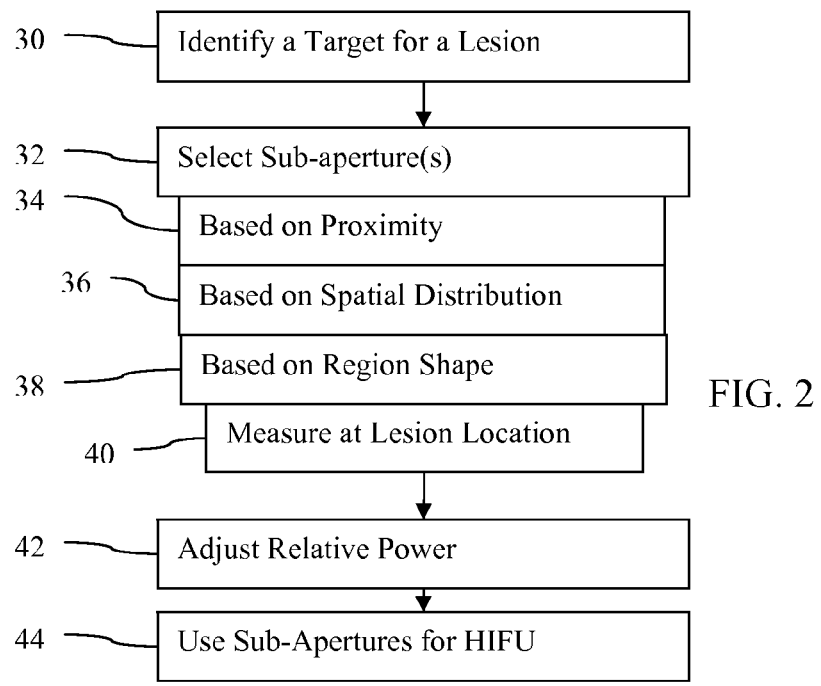
FIG. 2 is a flow chart diagram of one embodiment of a method for sub-aperture control for high intensity focused ultrasound.

FIG. 2 shows a method for sub-aperture control for high intensity focused ultrasound. The method uses the system 10 of FIG. 1, different transducers, different conformal arrays, and/or different systems. The acts are performed in the order shown or a different order. Additional, different, or fewer acts may be used. For example, the method is performed without acts 30, 42, and/or 44. As another example, the method includes at least acts 30, 32, and 36. In another example, the method includes at least acts 32 and 34, or acts 32 and 38, or acts 32 and 40, or combinations of act 32 with any of 34, 36, 38, and 40.

In act 30, one or more lesions are identified. To identify a lesion, image data representing the patient is acquired. One or more transducers are used to scan a region of the patient. For example, different regions are scanned by different sub-apertures or by an array. The transducer, such as a blanket ultrasound device or a conformal array, is placed on the patient. The imaging arrays of the ultrasound device or conformal array scan different, but overlapping regions of the patient. For example, different overlapping volumes are scanned with two-dimensional arrays. Other scans, such as with one array using one aperture, may be used.

To scan, acoustic energy is transmitted along a plurality of scan lines, and echoes are received in response to the transmission. The received echoes are converted into received electrical signals. The transmission and reception are performed for imaging, therapy, and/or testing possible paths. Alternatively, other imaging modes are used to acquire data representing the volume, such as MRI or CT data.

For ultrasound, the scan lines are formatted for scanning a plane or volume. A sector or other format scan may provide more overlap than a linear scan. In one embodiment, a dataset representing a three-dimensional volume is formed by transmitting and receiving. The dataset is formed by scanning an entire volume. Alternatively, different scans of overlapping volumes are performed, and the overlapping volumes are combined. Different transducers scan different, but overlapping volumes. The acquisition is triggered and the multiple volumes are streamed to an external or post-processing processor.

Alternatively, the scan lines correspond to possible treatment paths. For example, the transmit and receive beams are formed along scan lines intersecting the region to be coagulated and from available sources of the high intensity focused ultrasound, such as from different sub-apertures. One or multiple arrays may be used to form the beams along the desired scan lines.

Where image data is acquired from different sub-apertures or from an array moved to different positions, the data is aligned and combined into a dataset representing the volume. The ultrasound imaging system determines the spatial relationship of the voxels or data samples to the transducer, and the transducer position sensing provides the relative or absolute position of the transducer or transducers. This allows every voxel of each sonographic acquisition to be assigned a spatial position. During acquisition, the positions and/or orientations of the transducers are sensed. The transducer position at each acoustic window is determined for spatially aligning the resulting acquisition data. Alternatively, data correlation is used to align datasets without absolute position determination of the sub-apertures.

The target for a lesion is identified from the image data in act 30. The location of the lesion is identified. The location may be a point, area, or volume. In one embodiment, the outline of the lesion is identified in at least two dimensions, providing a size and shape of the lesion. The target for a lesion is any tissue abnormality, such as a possible cancerous growth, other undesired structure, or a hole in the circulatory system. Larger lesions may not be created by a single sonication. In this case, lesions may be divided into a number of smaller subsets, and each subset corresponds to the region covered by a one sonication. Same or different sub-apertures and dosing instructions can be used to treat different lesion subsets.

Manual, automatic, or semi-automatic identification is used. For example, the user selects a point in different views as indicating the location of a bleeding vessel or other lesion target. The geometric relationship of the different views may provide an indication of a location in a volume for treatment. As another example, a processor identifies a region for vascular closure of an internal hemorrhage. In yet another example, a processor, with or without user input of spatial locations, identifies the lesion target based on a tissue characteristic or border detection. An image process is performed to identify the lesion target (e.g., a leakage of a vessel). Any type of data may be processed, such as ultrasound, CT, X-ray, or MRI.

In one embodiment, ultrasound data representing the volume, such as acquired with a blanket ultrasound device, is used to localize a lesion target, such as a bleeder, with a processor. For example, Doppler information shows a flow pattern associated with bleeding or cancerous growth. As another example, B-mode data shows a tear or hole in a vessel wall or a nodule using boundary detection and high pass filtering of the boundary. In another example, power Doppler data is segmented to identify the locations of flow within a volume. In yet another example, acoustic force radiation is used to vibrate a vessel wall or other tissue. Differences in vibration results may indicate a location of bleeding or other type of lesion.

In act 32, at least one of a plurality of sub-apertures is selected for creating the lesion. The array includes a plurality of sub-arrays. Each sub-array is physically separate from the other sub-arrays, such as having different electrical connections and/or having a space between the outer edges of the arrays that is larger than the space between elements. Each sub-array is a different sub-aperture of the aperture used to create the lesion. Alternatively or additionally, the array is continuous and different sub-apertures are defined electrically, such as selecting different groups of elements to operate together. The sub-apertures may be programmed for different times or uses. For example, a continuous array is partitioned into sub-apertures with equal or un-equal spacing or sizes. Recursive zonal equal area sphere or other partitioning may be used. The number of zones desired is input, and sub-apertures using most or the entire array to provide the input number of zones are determined.

One or more of the possible sub-apertures are selected. For example, 5-10 sub-apertures out of a possible 20-30 sub-apertures are selected. Selecting the sub-apertures may distribute a heat load on skin or internal tissue not to be treated. Each selected sub-aperture is associated with a different path from the sub-aperture for the beam to travel to the lesion. All or a subset of one or more of the possible sub-apertures are selected.

Figure 3:
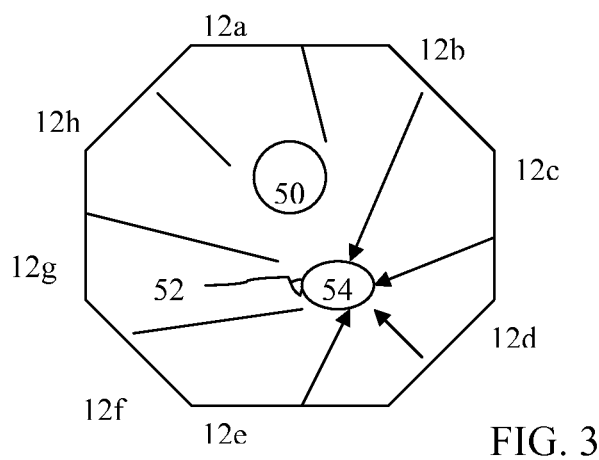
FIG. 3 is a graphical representation of different sub-apertures and their relationship with a lesion in a patient.

FIG. 3 shows HIFU transducers 12*a-h* surrounding a treatment region or lesion target 54. Adjacent the treatment region is a bone 50 and a piece of metal 52, such as associated with hemorrhaging due to metal fragments in a leg. Possible paths for treatment beams are represented by lines from each HIFU transducer 12*a-h* towards the treatment region 54. Each path is a straight line from the origins to the region to be treated within the patient, so corresponds to a scan line or beam volume for the transmission of an ultrasound treatment beam. For HIFU transducers 12*a* and 12*f-h*, the lines intersect or are close to the metal 52 or bone 50. To provide the desired power for coagulation or other treatment, the HIFU should not be transmitted into an obstruction. To prevent heating material that may cause further damage (e.g., the metal 52), paths intersecting or close to the material are not selected. The paths free of obstruction are selected, such as from HIFU transducers 12*b-e*. The obstructions may be detected by analysis of the image data. The selection is automatic or manual.

Other criteria for selection of sub-apertures may be used. The criteria may be spatial without characterizing tissue or the lesion (e.g., relative distances to lesion, proximity of lesion to one or more sub-apertures, and/or angle distribution). The criteria may be related to the lesion shape and/or size, such as selecting apertures to overlap in focal region to cover a desired portion (e.g., all) of the lesion while minimizing focal region extending beyond the lesion (e.g., minimizing collateral damage). The criteria may be based on feedback from testing transmissions, such as measuring temperature change or tissue displacement at the lesion based on separate, sequential transmissions and measurements for each sub-aperture and/or based on transmission and measurement from a group of sub-apertures (e.g., all or preliminary selected sub-apertures).

Combinations of these selection criteria may be used. The combination of criteria may use any function or be performed in any order. For example, each criterion is used to weight a value for each sub-aperture. The sub-apertures associated with a smaller value, larger value, or within a threshold limit are selected. In one embodiment, a sequential selection process is used. In a first order, sub-apertures are selected based on their spatial proximity to target, angular distribution of sub-apertures, and/or desired lesion shape without testing. Image data is used to select the sub-apertures, such as to determine the relative location of the target lesion to the sub-apertures and to determine the shape of the lesion. Further selection occurs in a second order process. Test transmissions are made in sequence or simultaneously from the sub-apertures selected in the first order. For this selection, some of the previously selected sub-apertures are deselected (i.e., sub-apertures of a further sub-set are selected).

Acts 34, 36, 38, and 40 represent different selection criteria. These acts are used alone or in combination.

In act 34, sub-apertures are selected based on spatial proximity of the sub-apertures to a lesion. Closer sub-apertures may operate with lower power at the array to provide the same level of treatment than farther sub-apertures, minimizing waste heat load in the patient, collateral damage and reducing input power consumption. The distance between the lesion and a center or other part of each sub-aperture is calculated. The distance may be determined from image data where the size of each voxel and relative positions of the arrays are known.

The spatial relationship of the HIFU transducers to the location to be treated is known or measured. For example, each HIFU transducer is rigidly mounted to an imaging transducer. The alignment of data from the different imaging transducers and the use of imaging data to identify the treatment region provide the spatial relationship of the HIFU transducer to the treatment region. As another example, the relative position of the HIFU transducer to the imaging transducer is measurable, such as with a strain gauge or other sensor. In another example, acoustic reflections from the HIFU transducer indicate the spatial relationship of the HIFU transducer to an imaging transducer. In another example, the HIFU transducer and imaging transducer are identified in a volume of MRI images, either by their natural border or by fiducial markers attached to the transducers. Combinations of these techniques or other techniques may be used.

A threshold is applied to the distance. Sub-apertures beyond the threshold distance are not selected, but closer sub-apertures are selected. For example in FIG. 3, the sub-apertures 12*b-f* are within a threshold distance and sub-apertures 12*a* and 12*g-h* are not selected. Sub-apertures that are physically close to the target are given priority, since less penetration and smaller steering angles may be used to reach the target.

Alternatively, the closest N sub-apertures are selected, where N is an integer set by the user, based on the array, based on a desired number of sub-apertures, or preprogrammed N may vary based on the distance of the lesion to the closest array. A smaller aperture is assigned to a shallow target; a larger aperture is assigned to deep target. For example in FIG. 3, apertures 12*d* and 12*e* are close to the lesion 54, so are the only two sub-apertures selected. Where the lesion is further from the sub-apertures, a greater number of sub-apertures are selected. For example, the array is not a cuff but instead is only around a part of a person's body, such as where only sub-apertures 12a-c and 12g-h are available. The sub-apertures 12a-c and 12g-h are spaced further from the lesion 54, so a greater number of sub-apertures are selected (e.g., selecting 12a-b and 12g-h).

In act 36, sub-apertures are selected based on angular distribution relative to the lesion. The sub-apertures are at different angles to the lesion. In the example of FIG. 3, the sub-apertures are generally at 20, 80, 135, 190, 260, 290, 305, and 350 degrees relative to the lesion 54. Sub-apertures with greater angular distribution may cause less beam overlap in regions outside the lesion. For example, sub-aperture 12a and 12h may have beam overlap near the lesion 54, but shallower and deeper, increasing the power applied to collateral, healthy tissue outside the lesion. By selected sub-apertures 12a and 12c instead, less overlap of the beams outside the lesion results. The sub-apertures are selected to have the beams cross or intersect at angles as great as possible.

Any function may be used for selecting based on angular distribution. For example, different rate or frequency of selection is used for different numbers of available sub-apertures. Where there are a large number of sub-apertures, every fourth or fifth sub-aperture is selected. Where there are fewer sub-apertures, every other or two out of every three sub-apertures are selected. A threshold angle difference may be used. For example, the sub-apertures are examined in sequence. If the next sub-aperture is associated with a beam intersecting a beam of the current sub-aperture by greater than a threshold angle, the sub-aperture is selected. If not selected, the angle for the current selected sub-aperture is compared with the angle for the next possible sub-aperture (e.g., compare angle for 12a with 12b, reject, and then compare 12a with 12c). Once another selection is made, that sub-aperture is used for comparisons to select the next sub-aperture.

Figure 4A:
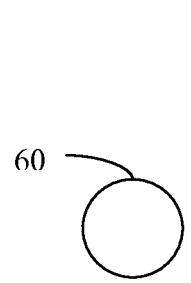
FIG. 4A is an example lesion.
Figure 4B:
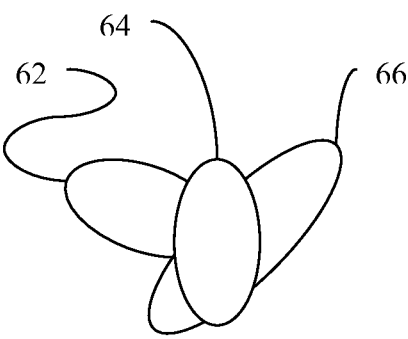
FIG. 4B is an example measured, focal distribution from three sub-apertures.
Figure 4C:
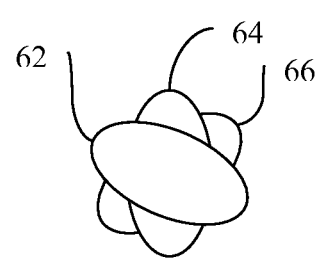
FIG. 4C is an example adjustment of the focal regions of the three sub-apertures based on the focal measurements.

In act 38, sub-apertures are selected based on a match of a region shape of a focus region provided by the selected sub-apertures to the lesion target. The lesion target has a size and shape, such as a spherical lesion target 60 represented in FIG. 4A. The focal regions of each sub-aperture have an elliptical, hour glass or other shape. FIGS. 4B and 4C show three elliptical focal regions 62, 64, 66. The focal region is determined by the intensity along the beam, such as a region defined by a certain amount (e.g., 6 dB or 12 dB) down from a peak. The focal region may be associated with the amount of power sufficient to contribute to treatment. Depending on the transmit settings, such as the location or depth of focus, the size or spatial extent of the sub-aperture, apodization, F#, or other information, the focal region for a given sub-aperture may have a different shape or size.

Since different sub-apertures cause focal regions at different angles, the combined focal region may have a different shape. For example, FIG. 4C shows three elliptical focal regions 62, 64, 66 overlapping to provide a star shaped focal region with greatest intensity at the overlapping regions centered on the lesion target 60. Other shapes may be provided, such as using different powers, focal depths, focus parameters to provide different focal region shapes for each component beam and a combination of a different shape. For example, FIG. 4B shows overlapping focal regions for a rotated "T" shaped lesion. Two, four, or other numbers of sub-apertures are selected to cover the lesion and minimize collateral damage. For example, the single focal region 64 is too narrow to cover the entire lesion target 60 of FIG. 4A, so three sub-apertures are selected to cover the lesion 60, as represented in FIG. 4C. If a particular shape of lesion target is desirable, multiple sub-apertures are selected and may be driven coherently or incoherently to approximate the target size and shape.

Simulation of the beam profiles given the spatial relationship of the lesion target to the sub-arrays guides the selection of sub-apertures.

In one embodiment, the proximity, angular distribution, and lesion target shape are used together for an initial selection of sub-apertures in act 32. The three criteria may be used sequentially, such as first selecting based on distance and then on lesion target shape with angular distribution used to resolve any selection where more than two combinations provide the desired lesion shape. The three criteria may be selected using a weighting function, such as weighting each sub-aperture based on each criteria, summing the weights, and selecting the highest weighted sub-apertures. The process may be iterative, such as weighting based on the three criteria, and then selecting the highest weighted sub-aperture. The weighting is applied again without the first selection available for selection but used to determine the weight for each criterion. A next sub-aperture is selected in each iteration. The final set may be tested to satisfy the desired lesion shape or other parameter. If the region shape does not match, then the process may be repeated with a different function, different weighting or limited in some other way. Fuzzy logic, degree of correlation, vector correlation, or other similarity measure may be used to select the apertures. One or more of the three criteria may be combined when they are related to the absorbed power around target lesion. Mapping of proximity, angular distribution, and lesion shape to absorbed power may be done through a lookup table. The lookup table is established through simulation and/or experimental characterization. The estimated absorbed powers from sub-apertures are superposed and integrated within a specified volume. Weights may be applied to different sub-aperture to achieve equal power. A maximization algorithm evaluates the integrated power and selects the optimal sets of sub-apertures.

In act 40, feedback from test transmissions are used to select one or more sub-apertures. The measured shape of the focal region is used for sub-aperture selection. Rather than simulating the focal region, the focal region shape is detected. One or more test transmissions are made from each sub-aperture and the resulting effect of the test transmission is measured. The region of effect for each sub-aperture indicates a focal region. As discussed above, the sub-apertures are selected to provide an overlapping focal region covering a desired portion or the entire lesion while minimizing collateral damage. A ratio of the volume of the lesion covered by the volume outside the lesion covered is maximized by grouping different sets of sub-apertures.

Before dosing starts, low dose sonications can be used to guide second order or original sub-aperture selection. For second order selection, only previously selected sub-apertures are tested. All or only a sub-set of these sub-apertures are selected. One or more previously selected sub-apertures may be deselected. The test transmissions are used for matching region shape and/or to verify targeting accuracy.

For measuring, test transmissions are performed from each of the sub-apertures. Each sub-aperture emits a low dose focused beam. All of the sub-apertures are tested or just sub-apertures previously selected using other criteria or approaches. The test transmissions are performed sequentially so that the effect of each sub-aperture may be measured. A sufficient interval of no transmission occurs between tests to allow the tissue to reach a steady state.

The test transmissions are from the sub-arrays of the treatment transducer. The test transmissions are at the same or different frequency, power, and/or duration as actual therapy transmissions. For example, a same frequency is used, but with less power and/or shorter duration. The transmission is sufficient to cause a measurable effect immediately (e.g., acoustic radiation force for causing a longitudinal or shear wave) or over time (e.g., change in temperature by 3 degrees or less).

The effect of the test transmission is measured. The lesion target and regions around the lesion target are scanned with an imaging transducer or the therapy transducer. Acoustic energy, such as for imaging, is transmitted along the same or different scan lines used for the test transmission. The signals representing the returning echoes are examined to detect the effect.

In one embodiment, tissue displacement is detected via acoustic radiation force impulse imaging (ARFI). Longitudinal or shear wave displacement caused by the test transmission is detected. A sequence of scans may be performed. The displacement from steady state over time is used to determine the maximum displacement for each location. The data from different times are correlated, such as using the minimum sum of absolute differences, to find the displacement in one, two, or three dimensions with or without consideration for rotation. The displacement may be measured as a distance, but may be determined in terms of velocity or time. In another example, the displacement may be determined as a set time after the acoustic force moves the tissue is measured. The set time is different for locations at different distances away from the focal point of application of the acoustic force.

In another embodiment, the change in temperature is measured. The resulting tissue temperature is measured by a tissue temperature detector. MR, ultrasound, or other thermometry is used. For ultrasound, one or more characteristics of the tissue are measured. The characteristics are input to a model. The model maps the characteristics to the tissue temperature. Since a change is measured, exact temperature estimation may not be needed.

The measurements are performed for a plurality of spatial locations. For example, the measurements are performed for an entire volume. As another example, the measurements are performed for locations within the lesion target, a subset of the lesion target, and locations within a set, programmed, or otherwise determined distance from the lesion target or the center of the lesion target. A region of interest set by the user or automatically may indicate the locations for which to measure the effect.

The sub-apertures may be selected based on the measurements. In one embodiment, the average of the measurements in the lesion target or a maximum value from inside the lesion target is used. If the value is below a threshold, then there may be an obstruction preventing the acoustic energy from sufficiently reaching the lesion target. For example, the temperature change from certain sub-aperture is less than one degree while temperature changes from adjacent sub-apertures are above three degrees. A threshold of one degree or other temperature change is used to include or not include sub-apertures. If the measurement, relative to measurements for other sub-apertures, has less effect, then the corresponding sub-aperture may be deselected.

The sub-apertures may be selected based on the spatial distribution of the measurements. Where the focal region of the sub-aperture does not sufficiently overlap the lesion target or where the focal region as measured includes tissue or structure to which therapy is not to be provided (e.g., metal fragments 52 or an organ), then the sub-aperture may be deselected. The sub-apertures are selected to avoid an acoustic obstruction, a heat sensitive region, a high attenuation region, scatterers, or combinations thereof that will be effected by the therapy as measured.

Other or different selection criteria may be used. For example, tissue along a path is heat sensitive, so the path is not selected. As another example, a path passes through more fluid and/or tissues with less attenuation, so is selected. One or more sub-apertures may be deselected due to a lack of acoustic window. For example, the ribs may block a sub-aperture. The sub-aperture is not selected. The blockage is determined from imaging data or from test transmissions. For example, an acoustic window is determined using a CT or MR image in a treatment planning stage. One or more sub-apertures are selected due to sufficient access to the lesion target from the exterior of the patient. The size and shape of each sub-aperture may be configured to a desirable window shape to avoid transmission into bone.

In act 42, the relative power to be provided by each of the selected sub-apertures may be adjusted. The power of none, just one, some, or all of the selected sub-apertures may be changed. The power is increased or decreased by altering the amplitude, frequency, duty cycle, or duration. By changing the power more or less for one sub-aperture as compared to other sub-apertures, the relative power contributed by the one sub-aperture is adjusted. To limit collateral damage, the power provided by each sub-aperture is more equal.

In one embodiment, a relative power of the selected sub-apertures is tuned as a function of a focal distribution. The focal distribution, such as measured in act 40 or acquired at a different time, is used to adjust relative power. The transmissions are performed for each sub-aperture with the same power, adjusted or not for depth attenuation. The detected results of the test transmission are used to scale the power from each sub-aperture. The average or peak temperature change or displacement caused by each sub-aperture is calculated. Other values may be used. These values represent relative contribution of each sub-aperture. For example, sub-apertures 12*c-e* have average temperature change of 2 degrees, 3 degrees, and 1 degrees, respectively. To equalize the sub-apertures, the power of sub-aperture 12*c* is weighted by 0.5, the power of sub-aperture 12*d* is weighted by 0.33, and the power of sub-aperture 12*e* is weighted by 1.0. Other weighting to provide equal, more similar, or more different relative power levels may be used.

In another embodiment, the power is adjusted to alter the shape of the focal region to match the lesion target. One focal region may be elongated relative to other focal regions, such as the focal region 66. Less attenuation or another factor may result in more power from a given sub-aperture. Focal region 64 for another sub-aperture is shown as expected. Focal region 62 for another sub-aperture is shown off-set towards (i.e., shallower) the sub-aperture, such as due to an aberration. The focus and/or power for each sub-aperture may be adjusted based on the detected focal region. For example, FIG. 4C shows the focal regions 62, 64, 66 scaled in power and changed in focus to a combined focal region which more closely covers the lesion target 60.

In another or additional embodiment, the selected sub-apertures, with or without further power adjustment, transmit test signals simultaneously or at a same time. Using the tissue displacement and/or temperature measurements, the resulting combined focal region is detected. The combined focal region may be altered to better match the desired lesion shape or to better avoid treating particular tissue. For example, with all selected sub-apertures transmitting at low dose, a detected 3D temperature map is used to tune each sub-aperture. The portion of the combined focal region caused by a given sub-aperture may be determined, such as based on the combined focal region have an elongated portion along a scan line from one sub-aperture through the lesion target. To achieve a desired focus shape, the relative power of the sub-apertures is adjusted. For example, the combined region appears as shown in FIG. 4B and is adjusted to provide a combined focal region as shown in FIG. 4C.

After the relative powers are adjusted, the HIFU transmit beams may be configured. Initial dosing parameters may be determined by a lookup table during treatment planning. The characteristics of the HIFU transmit beam or beams are determined by a processor, by a user, or combinations thereof. The characteristics include power, phasing, frequency, combinations thereof, and/or other characteristics (e.g., duration, sequence, or pulse repetition interval). The determination may be a function of the selected sub-apertures. For example, higher power pulses may be transmitted for a fewer number of paths. The determination is a function of the desired therapy or amount of power (i.e., dose) to be delivered in a specific period to cause coagulation or provide treatment. Any now known or later developed dosage considerations may be used for the HIFU beam or beams.

In one embodiment, the power and frequency of the high intensity focused ultrasound is determined, at least in part, as a function of a characteristic of the path. For example, the frequency of the high intensity ultrasound adapts as a function of depth from the HIFU transducer to the treatment region, attenuation characteristic along the path, or combinations thereof. The optimum HIFU frequency depends on the target depth, attenuation constant, the transmit transfer function of the transducer, and any limiting factor. Limiting factors may include, for example, maximizing the power absorption at the target depth or minimizing the power absorption at the skin. The frequency at which the acoustic intensity is highest may not be the optimum HIFU frequency because of the frequency dependence of the acoustic absorption. A desired or optimum HIFU frequency may be calculated given the target depth, and the tissue type between the target and the transducer. Image processing, thresholding, or other technique may be used to distinguish tissue type. For example, fluid, soft tissue and bone tissue types or structures may be distinguished. More subtle distinctions between types of soft tissue may be made. The different types are associated with different acoustic attenuation.

Tissue heating is achieved by absorption of acoustic power. Acoustic absorption is proportional to an attenuation coefficient. Higher attenuation provides higher acoustic power absorption and heat generation. Attenuation and absorption increase with frequency, so it is desirable to use higher frequencies for heating. However, higher propagation attenuation at higher frequencies means shallower penetration depth. There is a trade-off between penetration depth and frequency, and heat.

In addition or as an alternative, the power dose of the high intensity ultrasound from each of the selected sub-apertures is determined. The power dose may be determined as a function of tissues along the path, distance from the transducer to the treatment region, number of selected sub-apertures, frequency of the transmission, combinations thereof, or other factors. For example, different tissue types provide different attenuation. The different attenuation of the treatment region and the regions between the treatment region and the transducer may alter the power required for treatment. Greater attenuation along the path may require a higher power dose transmitted from the transducer. Greater absorption at the treatment region may require a lower power dose transmitted from the transducer. The power dose is altered by changing frequency, amplitude, duty cycle, and duration of the transmitted waveforms.

The contribution of each sub-aperture to the dose is determined. Equal contribution may be used. Alternatively, relative weighting determined by measuring the effects of the test transmission is used to set the transmit power. The contribution of each sub-array is set to match the weight. The dose for the lesion is divided between the sub-apertures based on the contribution of each sub-aperture determined in act 42.

In act 44, the selected set of the sub-apertures is used for the high intensity focused ultrasound. High intensity focused ultrasound is applied to the lesion target with the selected sub-apertures and not the other ones of the sub-apertures. The high intensity ultrasound is transmitted along one or more paths from the selected sub-apertures. The high intensity focused ultrasound is transmitted along the selected rays or scan lines. As more sub-apertures are provided, the HIFU power required for a given beam will be less due to total of the combined transmitted power.

The HIFU beams are transmitted from each selected sub-aperture at a same or substantially same time so that the power delivered at a given time at the treatment region is sufficient. Sequential transmission with different or the same sub-apertures or combinations of sequential and simultaneous may be used to provide the desired total power, temporally distributed power, and/or spatially distributed power.

The ultrasound energy is focused at the treatment region. If sufficient energy is radiated to the treatment region, cells located in the focal volume may be rapidly heated while intervening and surrounding tissues outside the focus are spared the same level of heating. Surrounding tissues are unaffected or affected less in the unfocused portion of the ultrasound beam because the energy is spread over a correspondingly larger area. The transmitted HIFU pulses have the determined frequency, power dose, or other characteristic.

The relative contribution of the sub-apertures may change during treatment. Feedback from a tissue temperature or displacement detector may be used to adjust dose on the fly. For example, the average temperature around the target, the shape of focus, or other information is used to identify a change. Actions include turning off sub-apertures, increasing or decreasing duty cycle at individual sub-aperture, and/or altering focus. The peak or averaged temperature around the focal spot can be used to guide dosing on and off time. If cavitations are detected, the power may be reduced from one or more sub-apertures. The detected shape of focus, if changing over time, may be used to guide power and focal pattern adjustment. For example, excessive heating towards the direction of certain sub-aperture indicates that the power from that direction is to be reduced.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for sub-aperture control for high intensity focused ultrasound, the system comprising:
    a phased array of elements, the array comprising an aperture;
    a sub-aperture circuit configured to activate and deactivate sub-arrays of the elements, the sub-arrays being sub-apertures of the aperture, each of the sub-apertures being less than all elements of the aperture;
    a processor configured to control the sub-aperture circuit so that the sub-aperture circuit is configured to select some of the sub-apertures and not select others of the sub-apertures, the selection being as a function of a distribution, at a target to be treated, measured with ultrasound transmissions from the sub-apertures; and a beamformer having channels configured to connect with respective elements of the sub-apertures and to separately beamform for each of the sub-apertures and not beamform for the others of the sub-apertures.

2. The system of claim 1 wherein the distribution is a measurement, at the target, of spatial distribution of temperature or strain change determined sequentially in time from each of the sub-apertures.

3. The system of claim 1 wherein the distribution is a measurement, at the target, of spatial distribution of tissue displacement determined sequentially in time from each of the sub-apertures.

4. The system of claim 1 wherein the processor is configured to weight a power of a first selected sub-aperture relative to a power of a second selected sub-aperture as a function of another distribution, at the target, measured with ultrasound transmission simultaneously from the first and second selected sub-apertures.

5. The system of claim 1 wherein the processor is configured to control the sub-aperture circuit so that the sub-aperture circuit is configured to select, and not select, as a function of a proximity of each of the sub-apertures to the target, an angle distribution of the sub-apertures to the target, and a shape of a focal region by transmission of ultrasound using a combination of the selected sub-apertures.

6. The system of claim 1 wherein the sub-aperture circuit is configured to select as a function of the measured distribution where the measured distribution is of focal regions of transmission of ultrasound from the sub-apertures.

7. The system of claim 1 wherein the processor is configured to simultaneously use at least two different sub-apertures to each treat with ultrasound at least two different targets.

* * * * *